United States Patent [19]  [11] Patent Number: 4,772,705
Schmiesing  [45] Date of Patent: Sep. 20, 1988

[54] PROCESSES FOR THE PREPARATION OF TRANS 1,3,4,6,7,11B-HEXAHYDRO-7-ARYL-2H-PYRAZINO[2,1-A]ISOQUINOLINES

[75] Inventor: Richard J. Schmiesing, Scottsville, N.Y.

[73] Assignee: Pennwalt Corporation, Philadelphia, Pa.

[21] Appl. No.: 759,022

[22] Filed: Jul. 25, 1985

[51] Int. Cl.$^4$ ............... C07B 37/10; C07D 487/04; C07D 241/04; C07D 241/08

[52] U.S. Cl. .................... 544/344; 544/384; 544/401

[58] Field of Search ......................... 544/344

[56] References Cited

U.S. PATENT DOCUMENTS 3,539,584 11/1970 Suh ........................... 544/133
3,557,120 1/1971 Archer ....................... 546/146
4,051,243 9/1977 Seubert ..................... 544/34 X
4,179,505 12/1979 Raymaekers ............... 514/253

OTHER PUBLICATIONS

Roderick et al, J. Med. Chem. 9, 181 (1966).
Maryanoff et al, J. Med. Chem. 27, 943–946 (1984).
Hirose et al, Chem. Abs. 89, 215207.
Vejdelek et al., Chem. Abs. 83, 97202.
Yoshizaki, Chem. Abs. 89, 129422f.

*Primary Examiner*—Mark L. Berch
*Attorney, Agent, or Firm*—Panitch Schwarze Jacobs & Nadel

[57] ABSTRACT

The trans isomeric form of 1,3,4,6,7,11b-hexahydro-7-aryl-2H-pyrazino[2,1-a]isoquinolines are prepared using novel 3-phenyl-4-arylacyl-2-piperazinones and 3-phenyl-4-(2-hydroxy-2-arylethyl) piperazines as intermediates. The process involves reacting a nove piperazinone with a reducing agent such as aluminum hydrides, borane or lithium borohydrides, and then reacting the resulting piperazine with a strong acid, such as polyphosphoric or sulfuric acid.

11 Claims, No Drawings

PROCESSES FOR THE PREPARATION OF TRANS 1,3,4,6,7,11B-HEXAHYDRO-7-ARYL-2H-PYRAZINOL[2,1-A]ISOQUINOLINES

CROSS-REFERENCE TO RELATED APPLICATIONS

The present application is related to copending patent application Ser. Nos. 086,000 filed Aug. 14, 1987 and Ser. No. 132,695, filed Dec. 14, 1987 which are respectively a division and a continuation of Ser. No. 759,019, filed July 25, 1985, now abandoned, all in the name of the same inventor, entitled "Processes and Intermediates Useful in the Preparation of Cis 1,3,4,6,7,11b-hexahydro-7-aryl-2H-pyrazino [2,1-a]isoquinolines.

BACKGROUND OF THE INVENTION

An efficient process for preparing the trans isomeric form of 1,3,4,6,7,11b-hexahydro-7-aryl-2H-pyrazino[2,1-a]isoquinolines is disclosed. The process involves the use of novel compounds, 3-phenyl-4-arylacyl-2-piperazinones and 3-phenyl-4-(2-hydroxy-2-arylethyl)piperazines.

SUMMARY OF THE INVENTION

The invention is, in part, the process of making the trans isomeric form of a compound of formula(1)

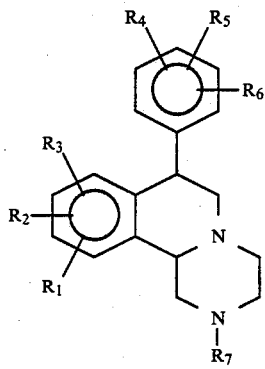

which comprises the steps of
(a) reacting a compound of formula (2)

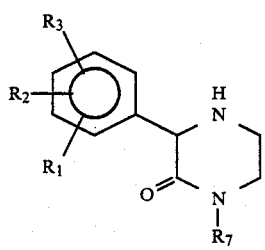

with a compound of formula (3)

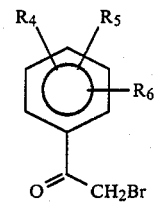

to form a compound of formula (4)

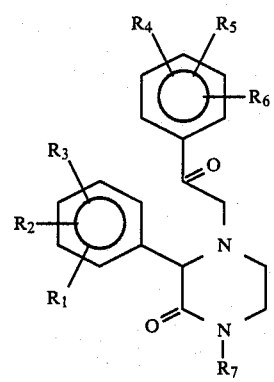

(b) reacting the compound of formula (4) with a reducing agent to form a compound of formula (5)

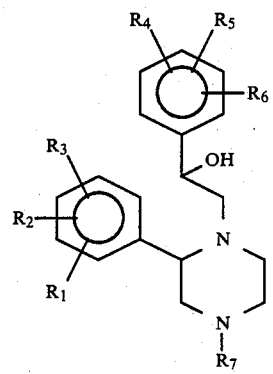

and (c) reacting the compound of formula (5) with a strong acid wherein, in Compounds (1),(2),(3),(4) and (5), $R_1$, $R_2$, $R_3$, $R_4$, $R_5$ and $R_6$ are independently hydrogen, halogen, hydroxy, amino, lower aminoalkyl, trifluoromethyl, lower alkyl, lower alkoxy, lower dialkylamino or lower monoalkylamino; and $R_7$ is hydrogen; provided that if $R_1$, $R_2$, $R_3$, $R_4$, $R_5$ or $R_6$ is amino, lower aminoalkyl, or lower monoalkylamino, then that amino, lower aminoalkyl, or lower monoalkylamino is protected in step (a).

The invention is additionally each individual step (a) or (b) of the above process.

The invention is also the process of making the trans isomeric form of a compound of formula (1) which comprises reacting a compound of formula (5) with a strong acid wherein, $R_1$, $R_2$, and $R_3$, are independently hydrogen, halogen, hydroxy, amino, lower aminoalkyl, trifluoromethyl, lower alkyl, lower alkoxy, lower dialkylamino, or lower monoalkylamino; $R_4$, $R_5$ and $R_6$ are independently hydrogen, halogen, hydroxy, nitro, amino, lower aminoalkyl, trifluoromethyl, lower alkyl, lower alkoxy, lower dialkylamino, lower monoalkylamino, or cyano; and $R_7$ is hydrogen or lower alkyl.

The invention is also the compounds of formula (4) and the compounds of formula (5).

In a subgeneric aspect of each of the above inventions, $R_2$, $R_3$, $R_5$ and $R_6$ are each hydrogen.

In a further subgeneric aspect of each of the above inventions, $R_1$ is substituted at the 3-position of the phenyl group in the compounds of formula (2), (4) and (5), and at the 10-position of the compounds of formula (1); and $R_4$ is substituted at the 4-position of the phenyl group in the compounds of formula (1), (3), (4) and (5).

DETAILED DESCRIPTION OF THE INVENTION

Definitions

"Lower aminoalkyl" is an amino group covalently linked to an alkyl group, straight or branched, containing one to seven carbon atoms.

"Lower monoalkylamino" is an alkyl group containing one to seven carbon atoms in a straight or branched chain, linked to an amino moiety.

"Lower dialkylamino" is two alkyl groups, each containing one to seven carbon atoms in a straight or branched chain, linked to an amino moiety.

"Lower alkyl" is an alkyl group containing one to seven carbon atoms in a straight or branched chain.

"Lower alkoxy" is an alkoxy group, containing one to seven carbon atoms in a straight or branched chain.

"Halogen" is either chlorine, fluorine, iodine, or bromine.

By the trans isomeric form of a 1,3,4,6,7,11b-hexahydro-7-aryl-2H-pyrazino[2,1-a]isoquinoline in the trans isomeric form is meant a compound of the formula (1)

in which the hydrogen atoms at the 7 and 11b positions of the molecule are on opposite sides of the plane of the ring that contains a single nitrogen atom. In the cis isomeric form, the hydrogen atoms at the 7 and 11b positions are on the same side of the plane of the ring that contains a single nitrogen atom.

Utility

The compounds of formula (1), in both their cis and trans isomeric forms, are useful because they have anti-depressant, anti-histaminic and cholinergic activities. Representative compounds of formula (1) are disclosed and discussed in U.S. Pat. No. 4,517,187.

The process of making the trans isomeric form of a compound of formula (1), the individual steps (a), (b) and (c) of that process, and the chemical intermediates [e.g., compounds of formula (4) and (5)] of that process, are useful in view of the utility of the compounds of formula (1).

Processes

The processes disclosed in the section, "Summary of the Invention" can be summarized in the following Scheme I:

Scheme I

-continued
Scheme I

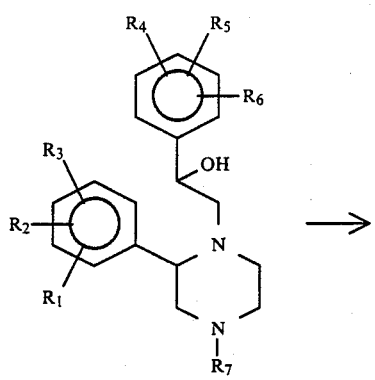
Procedure (c)

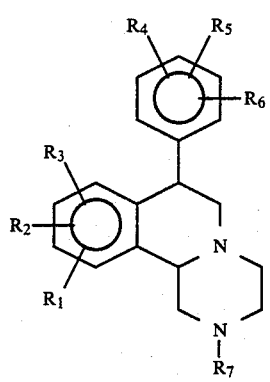

Preparation of 3-phenyl-2-piperazinones as starting materials

The 3-phenyl-2-piperazinones for use in Procedure (a) are prepared as reported in the literature [W. R. Roderick, H. J. Platte, and C. B Pollard; *J. Med. Chem.*, 9, 181(1966)[. This step allows for the use of ring-substituted ethyl α-bromophenylacetates, substitution which can be retained or chemically altered during the sequence of Scheme I. This particular advantage additionally implies the ready access to Formula I compounds regardless of whether $R_1, R_2$ and $R_3$ are the same or different (see also Procedure (a)).

Preparation of 3-phenyl-4-(2-hydroxy-2-phenylethyl)piperazines when one or more of $R_4, R_5$ and $R_6$ is nitro The 3-phenyl-4-(2-hydroxy-2-phenylethyl)-piperazines when one or more of $R_4, R_5$ and $R_6$ is nitro can be prepared for use in Procedure (c) by making the corresponding compound with one or more of $R_4, R_5$ and $R_6$ as amino and oxidizing the amino group to nitro by well known procedures.

Preparation of 3-phenyl-4-(2-hydroxy-2-phenylethyl)piperazines when one or more of $R_4, R_5$, and $R_6$ is cyano The 3-phenyl-4-(2-hydroxy-2-phenylethyl)-piperazines when one or more of $R_4$, $R_5$ and $R_6$ is cyano can be prepared for use in Procedure (c) by making the corresponding compound with one or more of $R_4, R_5$ and $R_6$ as halogen and converting the halogen to cyano by well known procedures.

Preparation of 3-phenyl-4-(2-hydroxy-2-phenylethyl)piperazines when $R_7$ is lower alkyl A 3-phenyl-4-(2-hydroxy-2-phenylethyl)-piperazine when $R_7$ is lower alkyl can be prepared for use in Procedure (c) by acylation of the corresponding compound that has $R_7$ as H to an amide followed by diborane reduction, in a manner analogous to the conversion of compound 11 to compounds 12a-e in Scheme II of R. C. Griffith et al, "Cis-1,3,4,6,7, 11b-Hexahydro-2-methyl-7-phenyl-2M-pyrazino[2,1-a]isoquinolines: A new atypical antidepressant,"to J. Medicinal Chemistry 1984, 27, 1995–2003.

Procedure (a) of Scheme I

Procedure (a) involves alkylation of a 3-phenyl-2-piperazinone with an equimolar amount of phenacyl halide in the presence of base. The base can either be an organic tertiary amine such as triethylamine or pyridine, or it can be an inorganic base such as an alkali carbonate or bicarbonate. A particularly useful base is potassium carbonate. The reaction is carried out at from 0° C. to 80° C. for 3–24 hours in an inert solvent such as chloroform, methylene chloride, dimethylformamide, acetone, toluene, or a lower alcohol, the halocarbon solvents being particularly convenient. The product is isolated by filtration of the reaction mixture and concentration of the filtrate. The product thus obtained is suitable for use in the next reaction without further purification, although a pure product may be obtained by recrystallization from an organic solvent.

Suitable protecting groups when one or more of $R_1, R_2, R_3, R_4, R_5$ and $R_6$ are amino, lower aminoalkyl, or lower monoaminoalkyl, are pthalimido, ethoxycarbonyl, benzyloxycarbonyl, and benzyl. After Procedure (a) has been completed, the protecting groups are readily removed by techniques such as hydrazinolysis, acid hydrolysis, or hydrogenolysis.

An advantage of Procedure (a) is that it allows for the use of a wide variety of readily available ring-substituted phenacyl halides as alkylating agents for analog preparation.

Procedure (b) of Scheme I

This procedure involves reacting the product of Procedure (a) with a reducing agent that will simultaneously reduce both the ketone and amide carbonyl portions of that product. Reducing agents with these properties include aluminum hydrides (preferably lithium aluminum hydride), borane, or lithium borohydrides [preferably lithium (tri-sec-butyl) borohydride]. The reaction is carried out in an inert solvent in which both the reducing agent and the product of Procedure (a) are soluble. Suitable solvents include: dioxane, diethyl ether, dimethoxyethane or tetrahydrofuran for lithium aluminum hydride and diborane; and tetrahydrofuran, hexane or diethyl ether for lithium (tri-secbutyl) borohydride. The reaction is carried out at from 20° to 80° C. for ether, dimethoxyethane, or tetrahydrofuran for 4–24 hours. The desired product, 3-phenyl-4-[2-hydroxy-2-(4-chlorophenyl) ethyl]-piperazine, for example, is isolated by employing common procedures known to those skilled in the art.

Procedure (c)

This procedure involves a Friedel-Crafts type cyclization of the products of Procedure (b) with a suitably strong acid; i.e., one strong enough to accomplish the cyclization. Preferred are suitably strong Bronsted acids, especially polyphosporic acid or sulfuric acid, and suitably strong Lewis acids. The reaction can take place either in the acid alone or in an inert solvent such as the aromatic hydrocarbons or aromatic halocarbons. For example, reaction in polyphosphoric acid at from 90° C. to 130° C. for several hours or in concentrated sulfuric acid at from 0° C. to 30° C. for 2–10 hours may be employed, the latter being particularly useful. The solid product [1,3,4,6,7,11b-hexahydro-7-(4-chlorophenyl)-2H-pyrazino [2,1-a]isoquinoline, for example,] is isolated by basification of the cooled reaction mixture with aqueous hydroxide followed either by filtration of the solid or by extraction with a suitable organic solvent such as the halocarbons dichloromethane or chloroform. In preferred embodiments of the reaction, yields greater than 95% can be obtained. Procedure (c) results in its product being substantially enriched (compared to its cis isomeric form) as to its trans isomeric form. A 19:1 trans:cis ratio of isomers is obtainable from the cyclization reaction. That ratio will increase as a result of the "work up" of the product, i.e., its solidification and crystallization.

EXAMPLES

The following examples are specific embodiments of the invention and are not limiting in any way.

EXAMPLE 1

Preparation of
3-Phenyl-4-(4chlorophenacyl)-2-piperazinone3-Phenyl-2-piperazinone To a stirred solution of 1928 g (32.1 mol) of ethylenediamine in 2 liters of absolute ethanol was added a solution of 3130 g (12.8 mol) of ethyl α-bromophenylacetate in 4 liters of absolute ethanol at such a rate so as to maintain reflux (~45 minutes addition time). The mixture was allowed to cool to ambient temperature and then concentrated to a thick yellow slurry. The slurry was stirred with 2 liters of chloroform, filtered, and the solid washed thoroughly with chloroform (total of 8 liters). The filtrate was concentrated to near dryness and the resulting residue stirred for a short time with 2 liters of isopropanol. The solid was collected by filtration, washed with 4 liters of isopropanol, and dried to give 1224 g (54%) of 3-phenyl-2-piperazinone. This material was used as such in the next step. [Pure material could be obtained by recrystallization from benzene and then from acetone to give a white solid (mp. 139.0°–139.5° C.).]

3-Phenyl-4-(4-chlorophenacyl)-2-piperazinone

A stirred mixture of 58.0 g (0.33 mol) of 3-phenyl-2-piperazinone, 85 g (0.62 mol) of blended potassium carbonate, and 76.9 g (0.33 mol) of 4-chlorophenacyl bromide in 400 ml of dichloromethane was heated at reflux for 12 hours. The mixture was cooled to ambient temperature, filtered, and the solid washed thoroughly with dichloromethane. The filtrate was concentrated to dryness, isopropanol added and stirred, the solid collected by filtration, washed thoroughly with isopropanol and dried in a vacuum oven at 50° C. to give 92.5 g (85 %) of 3-phenyl-4-(4-chlorophenacyl)-2-piperazinone. This material was used in Example 2 of the process. Pure material could be obtained by recrystallization from methanol to give a white solid (mp. 157°–158° C. dec.).

By following essentially the same procedure but substituting phenacyl bromide, 3-chlorophenacyl bromide, 3-hydroxyphenacyl bromide, 2-pthalimidophenacyl bromide, 2-(pthalimidomethyl)phenacyl bromide, 4-(trifluoromethyl) phenacyl bromide, 4-methylphenacyl bromide, 2-methoxyphenacyl bromide, 3-(N-ethyl-N-methylamino)phenacyl bromide, and 4-(N-methyl-N-benzylamino) phenacyl bromide for the 4-chlorophenacyl bromide above results in the formation of the following compounds, respectively:
3-phenyl-4-phenacyl-2-piperazinone (mp. 178°–180.5° C. dec), 3-phenyl-4-(3-chlorophenacyl)-2-piperazinone (mp. 152°–154.5° C. dec),
3-phenyl-4-(3-hydroxyphenacyl)-2-piperazinone,
3-phenyl-4-(2-pthalimidophenacyl)-2-piperazinone,
3-phenyl-4-[2-(pthalimidomethyl)phenacyl]-2-piperazinone,
3-phenyl-4-[4-(trifluoromethyl)phenacyl]-2-piperazinone,
3-phenyl-4-(4-methylphenacyl)-2-piperazinone,
3-phenyl-4-(2-methoxyphenacyl)-2-piperazinone,
3-phenyl-4-[3-(N-ethyl-N-methylamino)phenacyl]-2-piperazinone, and
3-phenyl-4-[4-(N-methyl-N-benzylamino)phenacyl]2-piperazinone.

By following essentially the same procedure but substituting
3-(2-chlorophenyl)-2-piperazinone,
3-(3-hydroxyphenyl)-2-piperazinone,
3-(2-pthalimidophenyl)-2-piperazinone,
3-[3-(pthalimidomethyl)phenyl]-2-piperazinone,
3-[4-(trifluoromethyl)phenyl]-2-piperazinone,
3-(2-methylphenyl)-2-piperazinone,
3-(3-methoxyphenyl)-2-piperazinone,
3-[4-(N-methyl-N-ethylamino)phenyl]-2-piperazinone, and
3-[2-(N-methyl-N-benzylamino)phenyl]-2-piperazinone for 3-phenyl-2-piperazinone, and phenacyl bromide for 4-chlorophenacyl bromide, results in the formation of the following compounds, respectively:
3-(2-chlorophenyl)-4-phenacyl-2-piperazinone,
3-(3-hydroxyphenyl)-4-phenacyl-2-piperazinone,
3-(2-pthalimidophenyl)-4-phenacyl-2-piperazinone,
3-[3-(pthalimidomethyl)phenyl]-4-phenacyl-2-piperazinone,
3-[4-(trifluoromethyl)phenyl]-4-phenacyl-2-piperazinone,
3-(2-methylphenyl)-4-phenacyl-2-piperazinone,
3-(3-methoxyphenyl)-4-phenacyl-2-piperazinone,
3-[4-(N-methyl-N-ethylamino)phenyl]-4-phenacyl-2-piperazinone, and
3-[2-(N-methyl-N-benzylamino)phenyl]-4-phenacyl-2-piperazinone,

EXAMPLE 2

Preparation of
3-Phenyl-4-[2-hydroxy-2-(4-chlorophenyl) ethyl]piperazine dihydrochloride To a suspension of 8.22 g (25.0 mmol) of 3-phenyl 4-(4-chlorophenacyl)-2-piperazinone in 25 ml of anhydrous tetrahydrofuran was added 150 ml of a 1.0M solution (150 mmol) of borane-tetrahydrofuran. The resulting mixture was heated at reflux for 18 hours, cooled to ambient temperature, and treated with dropwise addition of 15 ml of 2.5M aqueous hydrochloric acid. This mixture was heated at reflux for 3 hours, cooled to ambient temperature, and stirred for 2 hours. The resulting solid was collected by filtration, washed with 50 ml of tetrahydrofuran, and dried giving 10.9 g of the crude product as a white solid contaminated with boric acid. This material was used in Example 3 of the process.

By following essentially the same procedure but substituting 3-phenyl-4-phenacyl-2-piperazinone,
3-phenyl-4-(3-chlorophenacyl)-2-piperazinone,
3-phenyl-4-(3-hydroxyphenacyl)-2-piperazinone,
3-phenyl-4-(2-aminophenacyl)-2-piperazinone,
3-phenyl-4-[2-(aminomethyl)phenacyl]-2-piperazinone,
3-phenyl-4-[4-(trifluoromethyl)phenacyl]-2-piperazinone,
3-phenyl-4-(4-methylphenacyl)-2-piperazinone,
3-phenyl-4-(2-methoxyphenacyl)-2-piperazinone,
3-phenyl-4-[3-(N-ethyl-N-methylamino)phenacyl]-2-piperazinone, and
3-phenyl-4-[4-(N-methylamino)phenacyl]-2-piperazinone,
for the 3-phenyl-4-(4-chlorophenacyl)-2-piperazinone results in the formation of the following compounds, respectively:

3-phenyl-4-(2-hydroxy-2-phenylethyl)piperazine,
3-phenyl-4-[2-hydroxy-2-(3-chlorophenyl)ethyl]piperazine,
3-phenyl-4-[2-hydroxy-2-(3-hydroxyphenyl)ethyl]piperazine,
3-phenyl-4-[2-hydroxy-2-(2-aminophenyl)ethyl]piperazine,
3-phenyl-4-[2-hydroxy-2-[2-(aminomethyl)phenyl]ethyl]piperazine,
3-phenyl-4-[2-hydroxy-2-[4-(trifluoromethyl)phenyl]ethyl]piperazine,
3-phenyl-4-[2-hydroxy-2-(4-methylphenyl)ethyl]piperazine,
3-phenyl-4-[2-hydroxy-2-(2-methoxyphenyl)ethyl]piperazine,
3-phenyl-4-[2-hydroxy-2-[3-(N-ethyl-N-methylamino)phenyl]ethyl]piperazine, and
3-phenyl-4-[2-hydroxy-2-[4-(N-methylamino)phenyl]ethyl]piperazine.

By following essentially the same procedure but substituting 3-(2-chlorophenyl)-4-phenacyl-2-piperazinone,
3-(3-hydroxyphenyl)-4-phenacyl-2-piperazinone,
3-(2-aminophenyl)-4-phenacyl-2-piperazinone,
3-[3-aminomethyl)phenyl]-4-phenacyl-2-piperazinone,
3-[4-(trifluoromethyl)phenyl]-4-phenacyl-2-piperazinone,
3-(2-methylphenyl)-4-phenacyl-2-piperazinone,
3-(3-methoxyphenyl)-4-phenacyl-2-piperazinone,
3-[4-(N-methyl-N-ethylamino)phenyl-4-phenacyl-2-piperazinone, and
3-[2-(methylamino)phenyl]-4-phenacyl-2-piperazinone
for 3-phenyl-4-(4-chlorophenacyl)-2-piperazinone, results in the formation of the following compounds, respectively:

3-(2-chlorophenyl)-4-(2-hydroxy-2-phenylethyl)piperazine,
3-(3-hydroxyphenyl)-4-(2-hydroxy-2-phenylethyl)piperazine,
3-(2-aminophenyl)-4-(2-hydroxy-2-phenylethyl)piperazine,
3-[3-(aminomethyl)phenyl]-4-(2-hydroxy-2-phenylethyl)piperazine,
3-[4-(trifluoromethyl)phenyl]-4-(2-hydroxy-2-phenylethyl)piperazine,
3-(2-methylphenyl)-4-(2-hydroxy-2-phenylethyl)piperazine,
3-(3-methoxyphenyl)-4-(2-hydroxy-2-phenylethyl)piperazine,
3-[4-(N-methyl-N-ethylamino)phenyl]-4-(2-hydroxy-2-phenylethyl)piperazine, and
3-[2-(methylamino)phenyl]-4-(2-hydroxy-2-phenylethyl)piperazine.

EXAMPLE 3

Preparation of trans-1,3,4,6,7,11b-hexahydro-7-(4-chlorophenyl)-2H-pyrazino [2,1-a]isoquinoline dihydrochloride To 30 ml of concentrated sulfuric acid at 0° C. was added portionwise 8.50 g (26.8 mmol) of the 3-phenyl-4-[2-hydroxy-2-(4-chlorophenyl)ethyl]piperazine dihydrochloride from Example 2 over a period of 0.5 hour. The resulting mixture was warmed to ambient temperature, stirred for 2 hours, poured onto ice chips, and made basic with 50% aqueous sodium hydroxide. The resulting solid was collected, air dried, dissolved in 50 ml of absolute methanol, and made acidic with gaseous hydrochloric acid (pH 1). Addition of 50 ml of diethyl ether gave a white solid which was collected by filtration and washed with 50 ml of a 1:1 methanol/ether mixture to give 2.7 g (27%) of the product as a white solid (mp 265°–267° C. dec.) containing less than 1% of the corresponding cis isomer.

By following essentially the same procedure but substituting 3-phenyl-4-(2-hydroxy-2-phenylethyl) piperazine,
3-phenyl-4-[2-hydroxy-2-(3-chlorophenyl)ethyl]piperazine,
3-phenyl-4-[2-hydroxy-2-(3-hydroxyphenyl)ethyl]piperazine,
3-phenyl-4-[2-hydroxy-2-(2-aminophenyl)ethyl]piperazine,
3-phenyl-4-[2-hydroxy-2- [2-(aminomethyl)phenyl]ethyl]piperazine,
3-phenyl-4-[2-hydroxy-2-[4-(trifluoromethyl)phenyl]ethyl]piperazine,
3-phenyl-4-[2-hydroxy-2-(4-methylphenyl)ethyl]piperazine,
3-phenyl-4-[2-hydroxy-2-(2-methoxyphenyl)ethyl]piperazine,
3-phenyl-4-[2-hydroxy-2-[3-(N-ethyl-N-methylamino)phenyl]ethy]piperazine, and
3-phenyl-4-[2-hydroxy-2-[4-(N-methylamino)phenyl]ethyl]piperazine,
for the 3-phenyl-4-[2-hydroxy-2-(4-chlorophenyl)ethyl]piperazine dihydrochloride results in the formation of the following compounds, respectively:
trans-1,3,4,6,7,11b-hexahydro-7-phenyl-2H-pyrazino[2,1-a]isoquinoline dihydrochloride,
trans-1,3,4,6,7,11b-hexahydro-7-(3-chlorophenyl)-2H-pyrazino [2,1-a]isoquinoline dihydrochloride,
trans-1,3,4,6,7,11b-hexahydro-7-(3-hydroxyphenyl)-2H-pyrazino [2,1-a]isoquinoline dihydrochloride,
trans-1,3,4,6,7,11b-hexahydro-7-(2-aminophenyl)-2H-pyrazino [2,1-a]isoquinoline dihydrochloride,
trans-1,3,4,6,7,11b-hexahydro-7-[2-(aminomethyl)phenyl]-2H-pyrazino [2,1-a]isoquinoline dihydrochloride, trans-1,3,4,6,7,11b-hexahydro-7-[4-trifluoromethyl)-
  phenyl)-2H-pyrazino [2,1-a]isoquinoline dihydrochloride,
trans-1,3,4,6,7,11b-hexahydro-7-(4-methylphenyl)-2H-
  pyrazino [2,1-a]isoquinoline dihydrochloride.
trans-1,3,4,6,7,11b-hexahydro-7-(2-methoxyphenyl)-
  2H-pyrazino[2,1-a]isoquinoline dihydrochloride,
trans-1,3,4,6,7,11b-hexahydro-7-[3-(N-ethyl-N-
  methylamino) phenyl]-2H-pyrazino[2,1-a]isoquinoline dihydrochloride, and
trans-1,3,4,6,7,11b-hexahydro-7-[4-(N-methylamino)-
  phenyl]-2H-pyrazino[2,1-a]isoquinoline dihydrochloride,
Following the same procedure but substituting
3-(2-chlorophenyl)-4-(2-hydroxy-2-phenylethyl)piperazine,
3-(3-hydroxyphenyl)-4-(2-hydroxy-2-phenylethyl)piperazine,
3-(2-aminophenyl)-4-(2-hydroxy-2-phenylethyl)piperazine,
3-[3-(aminomethyl)phenyl]-4-(2-hydroxy-2-phenylethyl)piperazine,
3-[4-trifluoromethyl)phenyl]-4-(2-hydroxy-2-phenylethyl)piperazine,
3-[4-(trifluoromethyl)-4-(2-hydroxy-2-phenylethyl)piperazine,
3-(2-methylphenyl)-4-(2-hydroxy-2-phenylethyl)piperazine,
3-(3-methoxyphenyl)-4-(2-hydroxy-2-phenylethyl)piperazine,
3-[4-(N-methyl-N-ethylamino)phenyl-4-(2-hydroxy-2-phenylethyl)piperazine, and
3-[2-(methylamino)phenyl]-4-(2-hydroxy-2-phenylethyl)piperazine,
for the 3-phenyl-4-[2-hydroxy-2-(4-chlorophenyl)ethyl]piperazine dihydrochloride results in the formation of the following compounds, respectively:
trans-1,3,4,6,7,11b-hexahydro-7-phenyl-11-chloro-2H-
  pyrazino[2,1-a]isoquinoline dihydrochloride,
trans-1,3,4,6,7,11b-hexahydro-7-phenyl-8-hydroxy-2H-
  pyrazino[2,1-a]isoquinoline dihydrochloride and
trans-1,3,4,6,7,11b-hexahydro-7-phenyl-10-hydroxy-
  2H-pyrazino[2,1-a]isoquinoline dihydrochloride,
trans-1,3,4,6,7,11b-hexahydro-7-phenyl-11-amino-2H-
  pyrazino[2,1-a]isoquinoline dihydrochloride,
trans-1,3,4,6,7,11b-hexahydro-7-phenyl-8-aminomethyl-
  2H-pyrazino[2,1-a]isoquinoline dihydrochloride and
trans-1,3,4,6,7,11b-hexahydro-7-phenyl-10-aminomethyl-2H-pyrazino[2,1-a]isoquinoline dihydrochloride,
trans-1,3,4,6,7,11b-hexahydro-7-phenyl-9-trifluoromethyl-2H-pyrazino[2,1-a]isoquinoline dihydrochloride,
trans-1,3,4,6,7,11b-hexahydro-7-phenyl-11-methyl-2H-
  pyrazino [2,1-a]isoquinoline dihydrochloride,
trans-1,3,4,6,7,11b-hexahydro-7-phenyl-8-methoxy-2H-
  pyrazino[2,1-a]isoquinoline dihydrochloride and
trans-1,3,4,6,7,11b-hexahydro-7-phenyl-10-methoxy-
  2H-pyrazino[ 2,1-a]isoquinoline dihydrochloride,
trans-1,3,4,6,7,11b-hexahydro-7-phenyl-9-(N-methyl-N-ethylamino)-2H-pyrazino[2,1-a]isoquinoline dihydrochloride, and
trans-1,3,4,6,7,11b-hexahydro-7-phenyl-11-methylamino-2H-pyrazino[2,1-a]isoquinoline dihydrochloride.
The mixtures of 8-position and 10-position substituted compounds can be separated into their individual components by standard methods such as selective crystallization or chromatography (for example, silica gel chromatography).

EXAMPLE 4

Preparation of
trans-1,3,4,6,7,11b-hexahydro-2-methyl-7-(4-chlorophenyl)-2H-pyrazino [2,1-a]isoquinoline
dihydrochloride 2-phenylpiperazine To an ice-cooled stirred suspension of 25. g (0.66 mol) of lithium aluminum hydride in 2.6 liters of anhydrous ether was added in portions over 0.5 hour 30 g (0.17 mol) of 3-phenyl-2-piperazinone. The resulting mixture was heated at reflux for 20 hours and then cooled to 0° C. Isolation of the product by standard methods gave 23 g (83%) of 2-phenylpiperazine as an off-white solid (mp. 83°–85° C.).

1-Methyl-3-phenylpiperazine

To an ice-cooled stirred solution of 5.45 g (0.033 mol) of 2-phenylpiperazine and 5.3 g (0.53 mol) of triethylamine in 580 ml of acetone was added dropwise over 20 minutes a solution of 4.8 g (0.033 mol) of methyl iodide in 20. ml of acetone. The resulting mixture was stirred at 0° C. for 1 h and then allowed to gradually warm to ambient temperature over 3 hours. The residue obtained upon concentration of the reaction mixture was dissolved in 200 ml of ether and treated with a solution of methanol and ether saturated with gaseous hydrochloric acid to give 4.5 g (54%) of 1-methyl-3-phenylpiperazine dihydrochloride as a white solid.

1-Methyl-3-phenyl-4-(4-chlorophenacyl)piperazine

To a stirred mixture of 14.0 g (0.08 mol) of 1-methyl-3-phenylpiperazine and 20 g (0.2 mol) of triethylamine in 160 ml of tetrahydrofuran was added dropwise a solution of 18.2 g (0.08 mol) of 4-chlorophenacyl bromide in 55 ml of chloroform. The resulting mixture was stirred at ambient temperature for 3.5 hours, poured into 50% aqueous sodium bicarbonate and extracted with chloroform. The organic extracts were combined, washed with water and saturated sodium chloride and dried over sodium sulfate. The filtrate was concentrated to dryness to give 25 g of crude 1-methyl-3-phenyl-4-(4-chlorophenacyl) piperazine. This material was used as such in the next step of the process.

1-Methyl-3-phenyl-4-[2-hydroxy-2-(4-chlorophenyl)ethyl] piperazine

To a stirred solution of 25 g (0.076 mol) of the 1-methyl-3-phenyl-4-(4-chlorophenacyl) piperazine in 450 ml of ethanol was added in portions 2.9 (0.076 mol) of sodium borohydride. The resulting mixture was stirred at ambient temperature for 2 hours, poured into 50% aqueous sodium chloride and extracted with ethyl acetate. The organic extracts were combined, washed with water and saturated sodium chloride and dried over sodium sulfate. The resulting crude product obtained from concentration of the filtrate was subjected to rapid liquid chromatography on a silica gel column to give 16 g (60% overall) of 1-methyl-3-phenyl-4-[2-hydroxy-2-(4-chlorophenyl)ethyl]piperazine as a white solid.

Trans-1,3,4,6,7,11b-hexahydro-2-methyl-7-(4-chlorophenyl)-2H-pyrazino[2,1-a]isoquinoline
dihydrochloride To 35 ml of concentrated sulfuric acid at 0° C. was added portionwise 9.1 g (27.5 mmol) of 1-methyl-3-phenyl-4-[2-hydroxy-2-(4-chlorophenyl) ethyl]piperazine dihydrochloride over a period of 0.5 hour. The resulting mixture was warmed to ambient temperature, stirred for 2 hours, poured onto ice chips, and made basic with 50% aqueous sodium hydroxide. The resulting solid was collected, air dried, dissolved in 50 ml of absolute methanol, and made acidic with gaseous hydrochloric acid (pH 1). The resulting white solid which crystallized was collected by filtration, washed with cold methanol, and dried to give 7.5 g (78%) of product (mp 313°–315° C. dec) containing less than 1% of the corresponding cis isomer.

By following the same procedure but substituting
3-(2-chlorophenyl)-2-piperazinone, and
3-(3-hydroxyphenyl)-2-piperazinone
for 3-phenyl-2-piperazinone, results in the formation of the following compounds, respectively:
trans-1,3,4,6,7,11b-hexahydro-2-methyl-7-phenyl-11-chloro-2H-pyrazino[2,1-a]isoquinoline dihydrochloride,
trans-1,3,4,6,7,11b-hexahydro-2-methyl-7-phenyl-8-hydroxy-2H-pyrazino[2,1-a]isoquinoline dihydrochloride and
trans-1,3,4,6,7,11b-hexahydro-2-methyl-7-phenyl-10-hydroxy-2H-pyrazino[2,1-a]isoquinoline dihydrochloride.

Mixtures of the 8-position and 10-position substituted compounds can be separated into their individual components by standard methods such as selective crystallization or chromatography (for example, silica gel chromatography).

By following the same procedure but substituting phenacyl bromide,
3-chlorophenacyl bromide, and
2-hydroxy phenacyl bromide
for 4-chlorophenacyl bromide results in the following compounds, respectively:
trans-1,3,4,6,7,11b-hexahydro-2-methyl-7-phenyl-2H-pyrazino[2,1-a]isoquinoline dinydrochloride,
trans-1,3,4,6,7,11b-hexahydro-2-methyl-7-(3-chlorophenyl)-2H-pyrazino[2,1-a]isoquinoline dihydrochloride, and
trans-1,3,4,6,7,11b-hexahydro-2-methyl-7-(2-hydroxyphenyl)-2H-pyrazino[2,1-a]isoquinoline dihydrochloride.

Use of the procedures in Examples 1 to 4, but with an appropriate choice of reagents in which two or more of the R$_1$,R$_2$,R$_3$,R$_4$,R$_5$ and R$_6$ substitution groups are other than hydrogen, results in the corresponding multisubstituted final product.

What is claimed is:

1. The process of making the substantially all trans isomeric form of the compounds of formula (1)

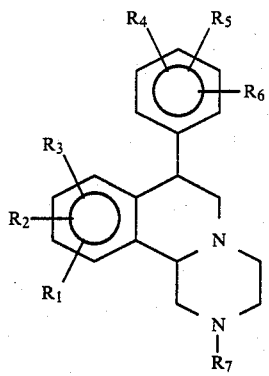

which comprises reacting a compound of formula (5)

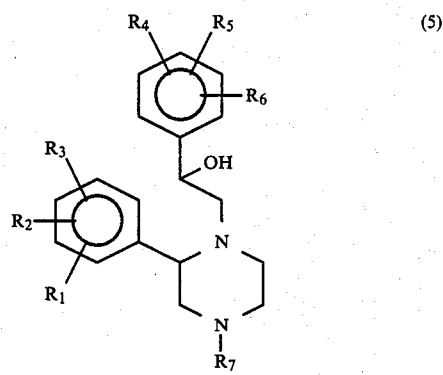

with a strong acid; wherein, in compounds (1) and (5), R$_1$, R$_2$, and R$_3$, are independently hydrogen, halogen, hydroxy, amino, lower aminoalkyl, trifluoromethyl, lower alkyl, lower alkoxy, lower dialkylamino, or lower monoalkylamino; R$_4$, R$_5$ and R$_6$ are independently hydrogen, halogen, hydroxy, nitro, amino, lower aminoalkyl, trifluoromethyl, lower alkyl, lower alkoxy, lower dialkylamino, lower monoalkyulamino, or cyano; and R$_7$ is hydrogen or lower alkyl.

2. The process of claim 1 wherein the R$_2$, R$_3$, R$_5$ and R$_6$ are each hydrogen.

3. The process of claim 2 wherein R$_1$ is substituted at the 3-position of the phenyl group of formula (5).

4. The process of claim 2 wherein R$_4$ is substituted at the 4-position of the phenyl group.

5. The process of claim 1 wherein said Bronsted acid is selected from the group consisting of polyphosphoric acid and sulfuric acid.

6. The process of claim 1 wherein the compounds of formula (5) are formed by reacting the compounds of formula (4)

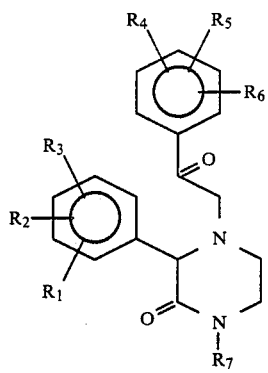

with a reducing agent.

7. The process of claim 6 wherein said reducing agent is selected from the group consisting of aluminum hydrides, borane and lithium borohydrides.

8. The process of claim 6 wherein the reaction is carried out in an inert solvent in which both the reducing agent and the compound of formula (4) are soluble.

9. The process of claim 6 wherein the compound of formula (4) is formed by reacting a compound of the formula (2)

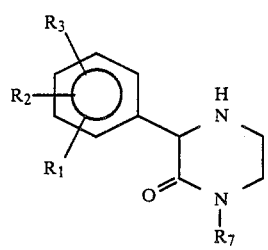

with a compound of formula (3)

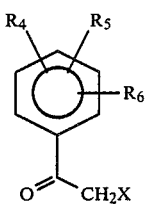

wherein X is a halide.

10. The process of claim 9 wherein the reaction of compounds (2) and (3) is carried out in the presence of a base.

11. The process of claim 10 wherein said base is potassium carbonate.

* * * * *